United States Patent [19]

Jarvis et al.

[11] Patent Number: 4,591,838

[45] Date of Patent: May 27, 1986

[54] SPILLAGE DETECTOR FOR LIQUID CHROMATOGRAPHY SYSTEMS

[75] Inventors: Michael R. Jarvis, Champaign; Donald S. Fulton, St. Joseph, both of Ill.

[73] Assignee: The United States of America as represented by the Administrator of the National Aeronautics and Space Administration, Washington, D.C.

[21] Appl. No.: 478,129

[22] Filed: Mar. 23, 1983

[51] Int. Cl.⁴ ............................................. G08B 21/00
[52] U.S. Cl. ................................. 340/605; 200/61.05; 141/198
[58] Field of Search .............. 73/61.1 C, 40; 340/605, 340/604; 141/198, 95, 88; 200/61.05; 251/7, 141

[56] References Cited

U.S. PATENT DOCUMENTS

| | | | |
|---|---|---|---|
| 3,200,388 | 8/1965 | Uhlig | 340/604 |
| 3,770,002 | 11/1973 | Brown | 200/61.05 |
| 4,043,906 | 8/1977 | Helmer | 73/61.1 C |
| 4,126,857 | 11/1978 | Lancia et al. | 340/605 |
| 4,259,985 | 4/1981 | Bergmann | 251/7 |
| 4,380,243 | 4/1983 | Braley | 73/313 |

Primary Examiner—James L. Rowland
Assistant Examiner—Jeffery A. Hofsass
Attorney, Agent, or Firm—Edward K. Fein; John R. Manning; Marvin F. Matthews

[57] ABSTRACT

A spillage detector device for use in conjunction with fractionation of liquid chromatography systems which includes a spillage receiving enclosure (34) beneath the fractionation area. A sensing device (36) having a plurality of electrodes (46) of alternating polarity is mounted within the spillage receiving enclosure (34). Detection circuitry (38), responsive to conductivity between electrodes (46), is operatively connected to the sensing device (36). The detection circuitry (38) feeds into the output circuitry (38). The output circuit has relaying and switching circuitry directed to a solenoid (60), an alarm system (118) and a pump (4). The solenoid (60) is connected to the pliable conduit (22) of the chromatography system. The alarm system comprises an audio alarm (190) and a visual signal (120). A 115-volt power system interconnected with the pump (4), the solenoid (60), the sensing device (36), and the detection and output circuitry (38).

10 Claims, 8 Drawing Figures

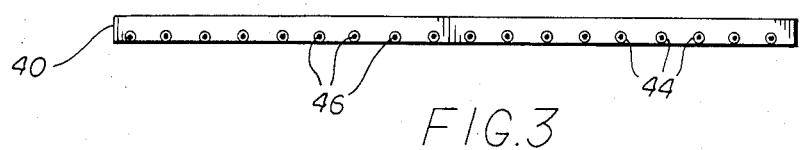
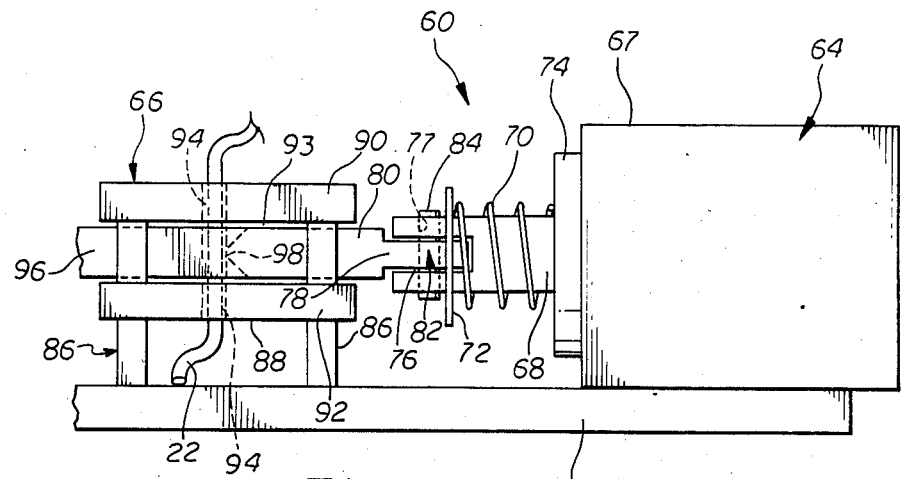
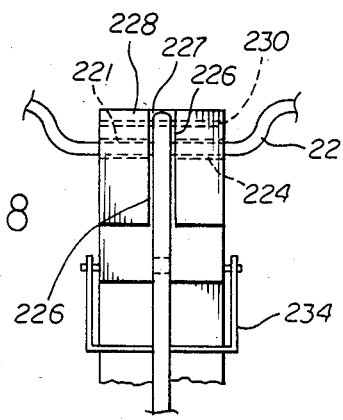
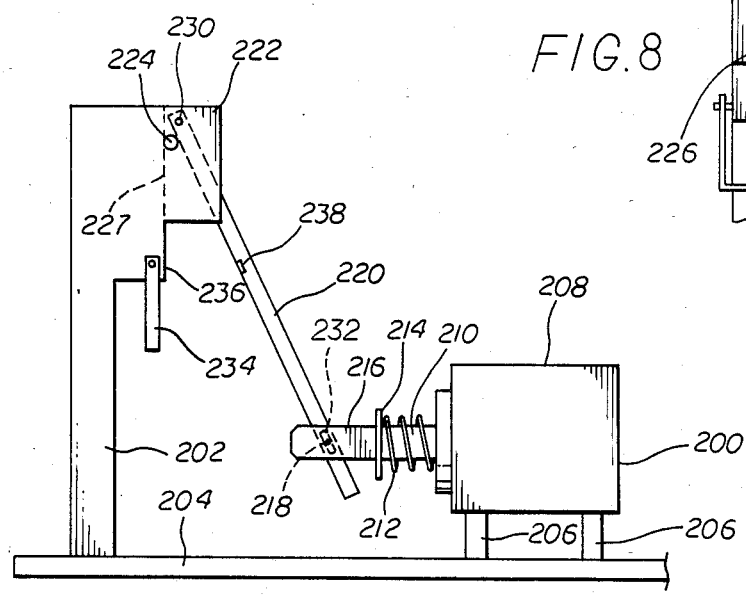

SPILLAGE DETECTOR FOR LIQUID CHROMATOGRAPHY SYSTEMS

ORIGIN OF THE INVENTION

The invention described herein was made in the performance of work under a NASA Contract, and is subject to the provisions of Section 305 of the National Aeronautics and Space Act of 1958, Public Law 85-568 (72 Stat. 435; 42 U.S.C. 2457).

TECHNICAL FIELD

The present invention pertains to devices for detecting the spillage of liquids. More particularly, it pertains to devices which detect sample spillage and prevent further spillage during the fractionation of liquid chromatography systems.

BACKGROUND ART

There are a number of devices which serve to detect the presence of water or other liquids. U.S. Pat. No. 4,227,190 discloses a water alarm for monitoring floor moisture. This uses a plurality of printed circuit sensor electrodes to detect the presence of moisture on a surface. If moisture is detected, a gating signal is created causing an alarm to issue a warning. U.S. Pat. No. 4,020,478 discloses a moisture detector wherein current flows between electrodes in response to the presence of moisture. U.S. Pat. No. 3,200,388 shows a water leakage alarm system for washing machines. Additionally, U.S. Pat. No. 2,127,538 is a signaling device for indicating the wetting of a bed or bed clothing by the occupant thereof. While all of the aforementioned patents provide a warning system to indicate the presence of a liquid, these inventions do not provide a positive action of preventing further leakage. As a result, these devices are not particularly useful for unattended liquid chromatography experiments.

Additional liquid sensing mechanisms are disclosed in U.S. Pat. Nos. 4,206,871 and 3,758,855. The former uses a vibration-sensing means to indicate leakage from a centrifuge. The latter shows a resistance controllable indicator wherein changes in electrical resistance caused by moisture contact results in variations in generated frequency.

Devices which shut off liquid flow upon the detection of moisture are also shown in the prior art. U.S. Pat. No. 4,297,686 relates to a resistant liquid detection and shut-off system providing protection from water damage. This device requires a resistive sensing circuit system. Furthermore, while this device uses a solenoid-operated water shut-off valve, it is not adaptable for the compressive closure of tubing. U.S. Pat. No. 3,874,403 describes a safety attachment for appliances subject to fluid leakage. This device employs a switch that includes a fluid responsive member to indicate the presence of liquid and to initiate the shut-off of fluid flow.

While the aforementioned patented devices may act to detect fluid spillage, they fail to preserve the effluent that is detected. In essence, these systems detect fluid spillage but fail to provide a means for preserving the fluid. Preservation of the spilled fluid can be important for the later continuation of the experiment. Essential data or sample can be omitted where the spilled fluid is removed or destroyed after detection. In addition, while the aforementioned patented devices may be useful in small experimental settings, they would not be particularly applicable to large-scale scientific or industrial liquid chromatography systems.

DISCLOSURE OF THE INVENTION

In the present invention, a fraction spillage detector device is disclosed which detects sample spillage and prevents further spillage during fractionation in liquid chromatography systems. The detector of the present invention utilizes a sensing device, having a plurality of electrodes of alternating polarity, to detect the presence of spillage. A detection circuit is operatively connected to the sensing device so as to be responsive to the spillage-created conductivity between the electrodes. Output circuitry is similarly operatively connected between the detection circuit, a solenoid apparatus, and an alarm system. The output circuitry effects a deactivation of the solenoid and an actuation of the alarm upon the presence of a liquid on the sensing device. The solenoid is in an arrangement so as to shut-off the liquid flow through the pliable conduit in the chromatography system. This solenoid shut-off device may be placed at any location relative to the flow through the system, since the stoppage of flow at any point will prevent continued spillage. The alarm is an audible alarm and/or a visual signal.

During the fractionation of liquids in a liquid chromatography system, there are occasional instances where the column outlet is not advanced to the next tube in the tube holder. This can result in overfill of a single tube and consequent spillage. In the present invention, the electrodes of alternating polarity are rendered conductive in the presence of liquid spillage. This conductivity causes the detection circuit to become active. The detection circuit initiates the signal which causes the output circuitry to deactivate the solenoid, thereby closing the pliable conduit. The output circuitry also switches to activate the alarm and deactivate the buffer pumps of the chromatography system. The present invention must be reactivated through a reset button before it permits the liquid in the column to resume flowing through the pliable conduit of the fractionator.

It is an object of the present invention to provide a device which is designed to detect liquid spillage during fractionation in liquid chromatography systems.

It is another object of the present invention to react to the detection of liquid spillage by closing the conduit from the column to the fractionator and by deactivating the buffer pumps of the system. This prevents loss, dilution, or contamination of material by preserving it in the column.

It is a further object of the invention to activate an alarm when the sensing device detects the presence of spillage from the fractionator. This serves to signal persons of the malfunction in the chromatography system.

The above and other objects of the present invention will become apparent from the drawings, the description given herein, and the appended claims.

BRIEF DESCRIPTION OF THE DRAWINGS

FIG. 3 is a side elevation of the spillage receiving area and sensing mechanism;

FIG. 4 is a side elevation in partial section of the shut-off device including the solenoid and the conduit;

FIG. 7 is a side elevation of an alternative embodiment of the shut-off device of FIG. 4; and FIG. 8 is a front view of a portion of the shut-off device as shown in FIG. 7.

DESCRIPTION OF A PREFERRED EMBODIMENT

Figure 1:
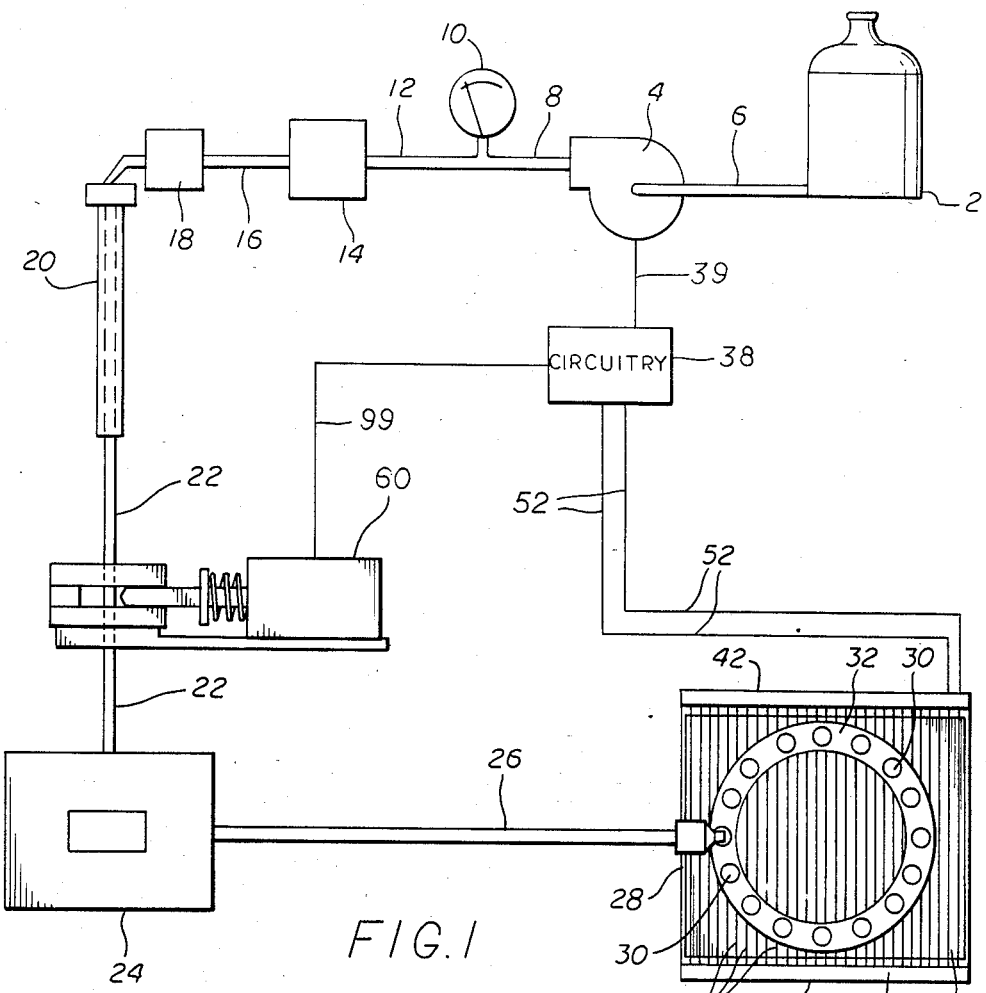
FIG. 1 is a general schematic representation of a liquid chromatography system showing the position of the fraction spillage detector in the system.

Referring first to the general schematic diagram of FIG. 1, the fraction spillage detector of the present invention comprises spillage receiving means 34 for collecting spillage from the fractionator, sensing means 36 within the receiving means, and the shut-off arrangement 38 including detection circuitry means, output circuitry means, and solenoid means. The location, operation, and function of these elements of the present invention in relation to the liquid chromatography system of FIG. 1 will be explained more fully hereinafter. While the fractionator in FIG. 1 is of an older variety, it is believed that this illustration is a simple and understandable presentation of liquid chromatography systems in general.

Chromatography is a method of separating substances that is widely used in analytical and preparatives chemistry. This method also has widespread applications in such fields as biochemistry, microbiology, cell biology, and laboratory techniques in diagnostic laboratories. Chromatography is commonly understood to involve the flow of a liquid or a gas over a solid or liquid stationary phase. A basic liquid chromatography system is shown schematically in FIG. 1. This representation is not meant to limit the scope of the invention since liquid chromatography systems take many forms, such as ion exchange, gel filtration, and affinity chromatography. FIG. 1 simply illustrates the elements of liquid chromatography that have relevance in this fraction spillage detector invention.

Initially solvent is contained within reservoir 2. There are many different types of reservoirs used in liquid chromatography. Simple reservoirs may be constructed from glass flasks or bottles of appropriate size. Reservoirs may also be made from stainless steel, which is inert to most mobile phases and is not subject to breakage. Buffer pump 4 pumps the solvent from reservoir 2 through fluid line 6. There are two types of pumps which may be used in liquid chromatography: mechanical constant-volume pumps and pneumatic constant-pressure pressure pumps. In the mechanical constant-volume pump, each stroke of the pump plunger (not shown) pushes a small volume of the mobile phase of the solvent into the chromatographic system. On the reverse stroke, the piston cavity refills from the reservoir 2 as a result of a ball-check valve system (not shown). The pump 4 pushes the solvent through conduit 8 to pressure gauges 10. Bourdon tube pressure gauges are the most commonly used devices for pressure measurement in chromatographic systems. From the pressure gauges 10, the solvent passes through line 12 to filtering forecolumn 14. This filtering forecolumn 14 is a short column, packed like main column 20, and located directly ahead of the main column. This forecolumn 14 is valuable as a filter for components of the solvent that are not eluted. The solvent passes through tube 16 from forecolumn 14 to injection device 18. The injection device 18 serves to add the sample to the mobile phase. This may be by either syringe injection through a septum or by valve injection.

The liquid flows directly from injection device 18 to the top of the main chromatographic column 20. Chromatographic column 20, usually made of glass, is held vertically and is uniformly packed with a sorbent. In other arrangements, chromatography column 20 may be applicable to molecular sieves, ion exchanges, affinity matrixes and other systems. A chromatogram is developed by passing one or several solvents through the porous bed in the column. The developing solvent produces a series of zones in the sorbent. The resulting effluent leaves column 20 and passes through pliable conduit 22 to detector 24. The detector 24 continuously monitors the components of the effluent stream. The detector 24 may be of the universal variety, which responds to all types of compounds, or of the selective variety, which gives little or no response to certain types of materials. This detector 24 analyzes the components of the effluent stream and provides the appropriate signals for fractionating the effluent. Detector 24 may also be of the type that counts drops or responds to the volume of fluid flow passing therethrough. Other types of detectors are responsive to elapsed time. The type of detector employed in the present liquid chromatography system is not critical to the embodiment of this invention. Thus, it is not intended as a limitation on the present invention.

The effluent flows from detector 24 through feed line 26 to fractionator 28. Although FIG. 1 shows one type of fractionator, it is important to realize that the present invention is useful for all types of fractionating devices. As shown in FIG. 1, a series of tubes 30 are contained in a rotatable tube holder 32. The tube holder 32 includes an indexing feature which responds to the signal produced by the detector 24. When the detector senses a different compound, component or volume of the effluent, the tube holder indexes so that a different tube 30 is in proper position to receive the liquid from feed line 26. Thus, the components of the effluent are collected sequentially by the tubes 30 in the fractionator. While this description illustrates one type of fractionator, the present invention is also useful in combination with a Gilson Microfractionator, which fractionates on the basis of fluid drop number or time. The Gilson Microfractionator is a very common device employed in liquid chromatography systems.

As stated previously, the present invention is shown in combination with the chromatography system of FIG. 1. Spillage receiving means 34, to be described hereinafter, is an enclosure positioned beneath tubes 30 and holder 32. Sensing means 36 extends about the length of the receiving means 34. In this embodiment, the tube holder 32 may be positioned in such a manner so as to not be conductive with the sensing means. This may be accomplished by either suspending the fractionating device from above the spillage receiving means or to support the fractionator with legs extending from beyond the width of the receiving means.

The sensing means 36 is operatively connected to the shut-off apparatus 38. This shut-off apparatus 38 includes the detection circuitry, the output circuitry, and the solenoid-operated shut-off device. The shut-off apparatus 38 is positioned about the pliable conduit 22 between the main column 20 and the detector 24. The shut-off apparatus 38 may also be positioned at any other location relative to the fluid flow in the liquid chromatography system. This apparatus is also operatively connected to the pumps 4 by electrical cable 39. The shut-off apparatus and its functions will be described more completely hereinafter.

Figure 2:
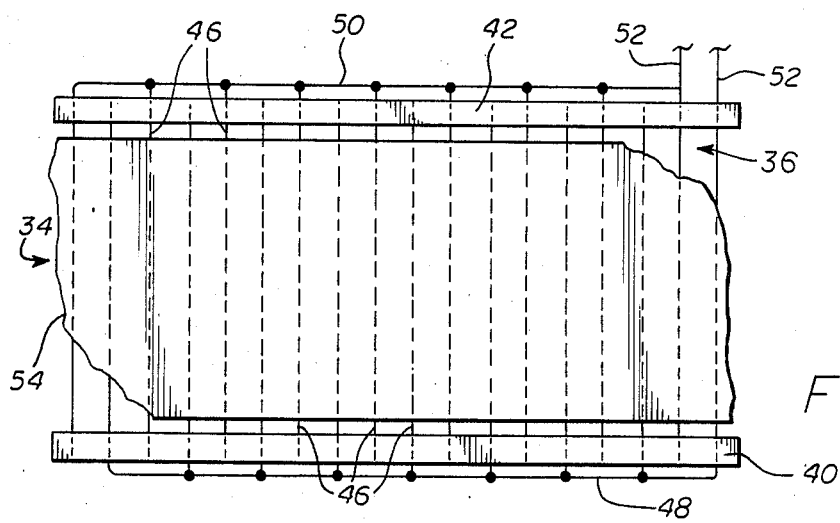
FIG. 2 is a top view of the spillage receiving area and sensing mechanism.

FIGS. 2 and 3 depict the spillage receiving means 34 and the sensing means 36. The spillage receiving means comprises an enclosure made of a pair of Lucite strips 40 and 42 extending along the length of the receiving means. Each of these strips has boreholes 44 for accommodating the sensing means. The Lucite strips 40 and 42 should be of sufficient length to accommodate the potential spillage area from the fractionator.

Sensing means 36 is located within the spillage receiving means 34. The sensing means 36 has electrodes 46 extending between strips 40 and 42. Each electrode 46 is a stainless steel rod. The electrodes 46 have their ends fitted into boreholes 44 of the receiving means. As seen in FIG. 3, the rods are positioned toward the bottom of the receiving means, these electrodes should be of sufficient length to cover the potential spillage area from the fractionator. Wires 48 connect every other electrode along one side of the receiving means. Wires 52 connect the remaining electrodes 46 on the other side of the receiving means. This wiring arrangement establishes alternating electrodes of opposing polarity within sensing means 36. Wires 52 connect the sensing means 36 to the detection circuitry of shut-off apparatus 38. Electrodes 46 are covered with filter paper 54 for enhanced sensitivity and conductivity. If there is a possibility that distilled water or other non-conductive liquid will be one of the liquids fractionated from the effluent, then it may be necessary to impregnate the filter paper 54 with salt so that adequate conductivity between the electrodes 46 will be assured.

The solenoid means 60, as included within shut-off device 38, is specifically shown in FIG. 4. Base 62 supports solenoid 64 and tube clamping channel 66. Solenoid 64, in this embodiment, is of the Guardian 4HD-CON%-11OD variety. Solenoid 64 includes housing 67, movable core 68, spring 70, and washer 72. Washer 72 is fixedly attached toward the end of core 68. Spring 70 is interposed between the washer 72 and the end 74 of solenoid housing 67. The spring exerts a force tending to pull core 68 outward when the solenoid is deactivated. When activated, as shown in FIG. 4, the magnetic coil within the housing 67 will draw the core inwardly. The core 68 has a channel 76 extending across the diameter of the core and an aperture 77 also extending through the core. Aperture 77 extends transversely in relation to channel 76. Channel 76 is of such a size as to accommodate the end 78 of plunger 80. End 78 of plunger 80 has a pin hole 82 extending therethrough so as to coincide with aperture 77 of core 68. Pin 84 is fastened to core 68 and plunger 80 through aperture 77 and pinhole 82. This couples the plunger to the solenoid in such a manner that any solenoid movement is translated to the plunger.

Tube clamping channel 66 is attached to base 62 by legs 86. The frame 88 of clamping channel 66 is rigidly mounted to legs 86. Frame 88 includes upper and lower members 90 and 92, respectively. Legs 86, upper member 90, and lower member 92 form a passageway 93 to guide the movement of plunger 80. Upper and lower members 90 and 92 also have a borehole 94 extending vertically therethrough. Borehole 94 permits the column effluent conduit 22 to pass therethrough. Column effluent conduit 22 must be pliable in that portion which passes through tube clamping channel 66. An interior member 96 is rigidly attached to legs 86 and frame 88. This interior member acts as a stop for plunger 80 on the opposite side of conduit 22 from plunger 80. Plunger 80 has a parabolic end 98 in passageway 93. The parabolic end 98 and interior member 96 cause pliable conduit 22 to be pinch-closed upon the inward movement of plunger 80. Solenoid means 60 is electrically connected to the detection circuitry through line 99. Thus, the solenoid means 60 acts to shut-off the liquid conduit whenever solenoid 64 is deactivated.

Figure 5:
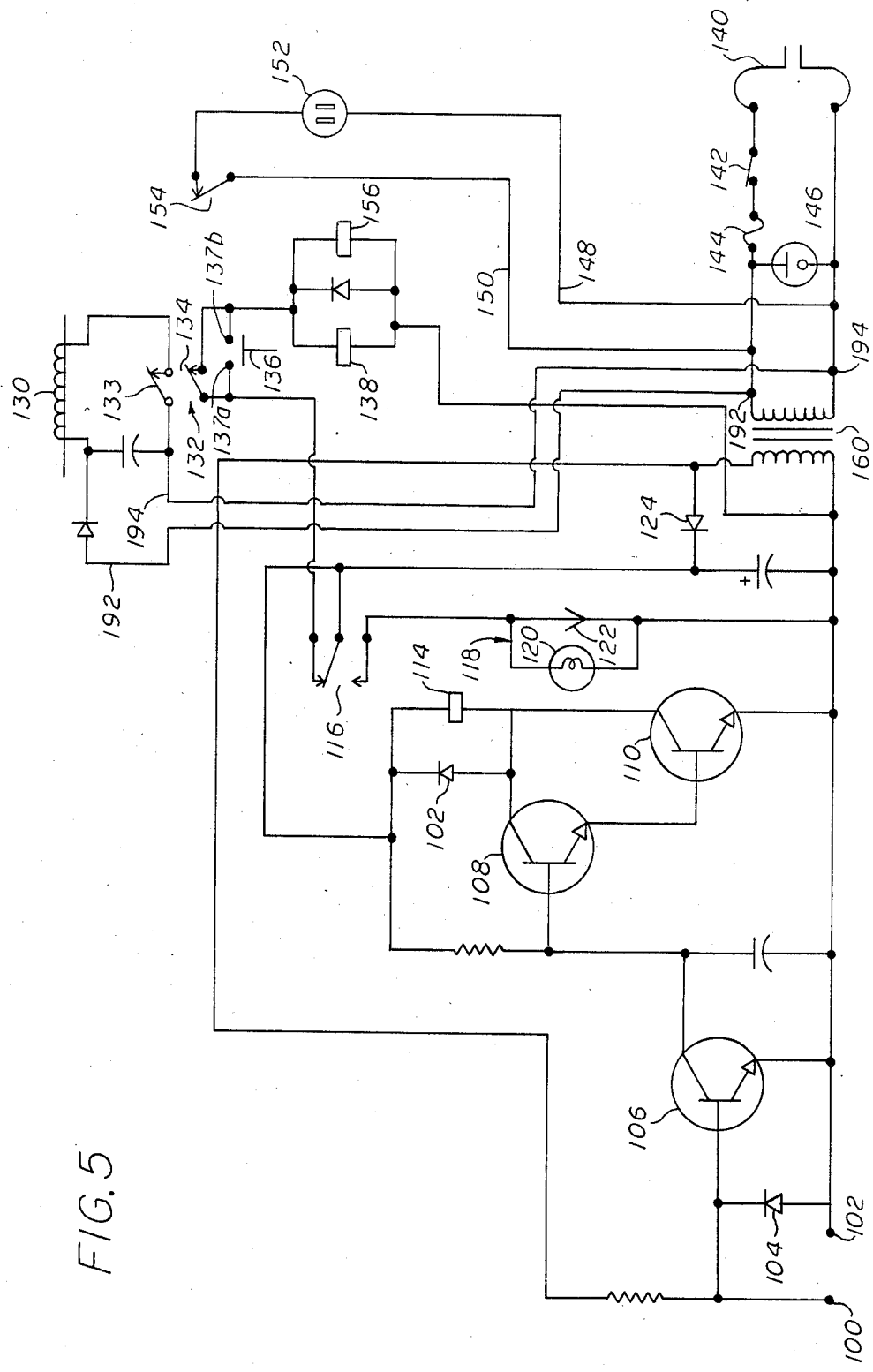
FIG. 5 is a schematic representation of the detection and output circuitry of the fraction spillage detector.

The detection and output circuitry means are schematically depicted in FIG. 5. FIG. 5 shows the normal operation of the circuits where there is no spillage from the fractionator upon the sensing means. The detection circuitry is connected at points 100 and 102 to the wires 52 extending from sensing means 36. Point 100 receives the positive polarity of the electrodes 46 of the sensing means 36. Point 102 receives the negative polarity of electrodes 46. In the absence of moisture or liquid in sensing means 36, no current flows between the electrodes 46, thereby making the circuit non-conductive. A semiconductor diode 104 receives the signal from point 102, rectifies the signal, and passes only the positive portions thereof to n-p-n transistor 106. In the absence of spillage, transistor 106 is conducting and continues the base circuit without turning on the collector circuit. Moisture at the electrodes 46 creates a partial shunt to be placed across semiconductor diode 104 and the base of transistor 106. This shunt causes transistor 106 to be cut off, thereby causing the collector circuitry to activate the detection system.

Transistor 106 is directly coupled to n-p-n transistor 108 such that when transistor 106 is cut off, transistor 108 is activated as part of the collector circuit. Transistor 108 is connected in a Darlington pair to n-p-n transistor 110. This arrangement, while consisting of two discrete transistors, operates as if it were a single transistor. Since the emitter of transistor 108 is connected directly to the base of transistor 110, the same current flows in both emitter-base circuits. The signal current entering transistor 108 is amplified by it, and then again by transistor 110, so that the total amplification is the product of the two transistors. This enables the alarm, the relays, and the switches to be adequately powered by the weak signal from the electrodes.

Figure 6:
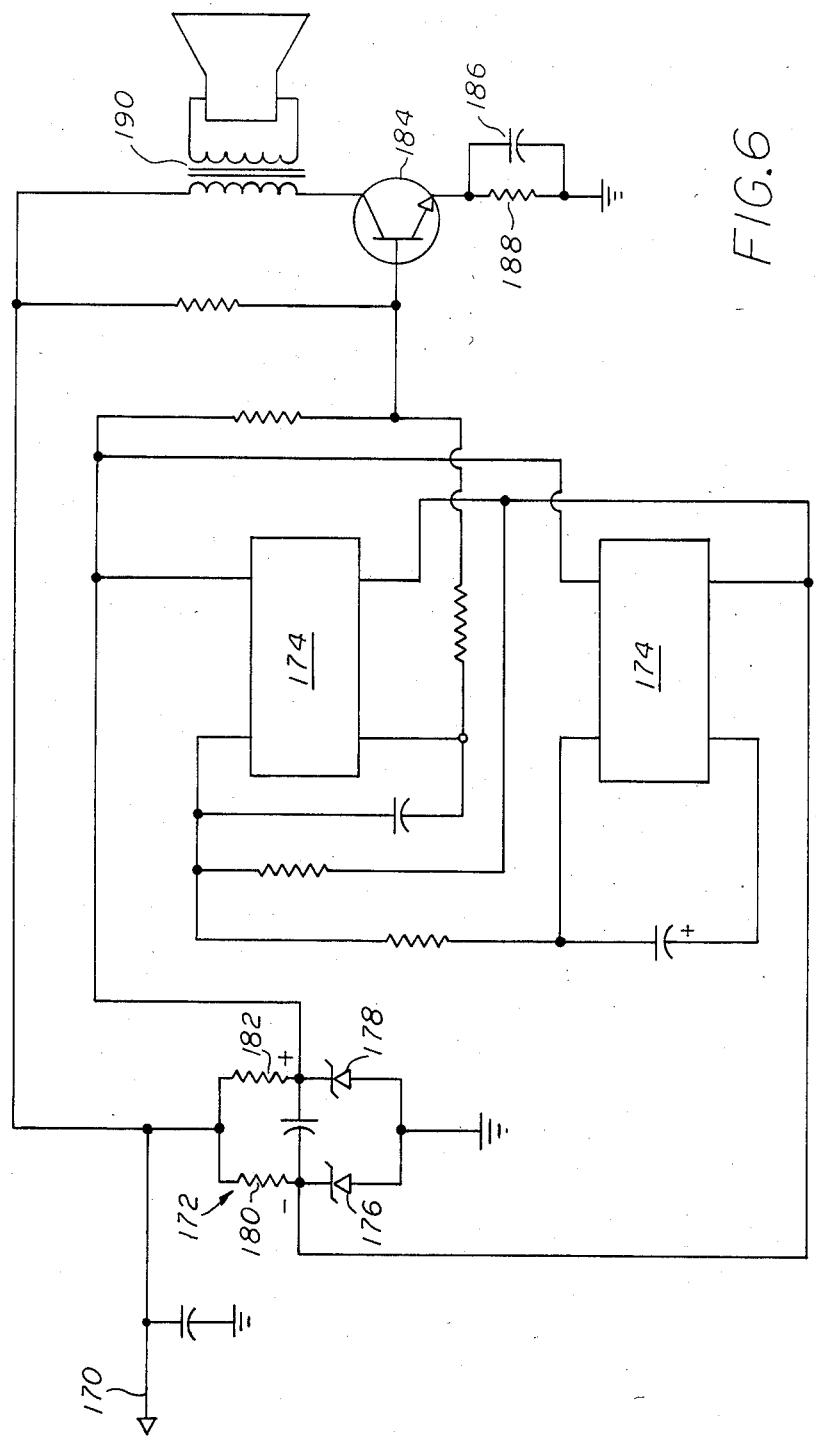
FIG. 6 is a schematic representation of an audio alarm for the spillage detector.

The collector of transistor 108 is joined to semiconductor diode 102 and relay 114. The collector of transistor 110 is similarly connected to relay 114. Relay 114 transmits a signal to double-throw switch 116. Switch 116 is the relay contacts for relay 114. In the absence of moisture in the sensing means, the switch will be normally positioned so as to touch the upper contact, as indicated on FIG. 5. As a result, the alarm 118 is deactivated. Alarm 118 includes glow lamp 120 and jack 122. Jack 122 is designed to receive the plug from the audio alarm, as schematically shown in FIG. 6.

Diode 124 extends between the line from switch 116 and the line to the positive electrodes in the sensing means. Diode 124 is a half-wave rectifier which changes the alternating current from the power source and the transformer into direct current for use by the electronics of this detector.

In normal operation, in the absence of moisture, the solenoid circuit 130 will have current flowing through it. The movable core is retracted within the solenoid housing 67 when the solenoid circuit is charged. As seen in FIG. 5, the two pole switch 132 is the contact assembly for relay 138. Switch 132 is normally closed. Both portions of the two pole switch 132 operate simultaneously in the same direction. The uppermost portion 133 of the two pole switch closes the solenoid circuit 130. When that portion of the switch is open, the circuit is broken and the solenoid circuit 130 is deactivated. The lower portion 134 of the two pole switch 132 maintains the relay circuit keeping both contacts 133 and 134 closed until moisture or a power failure disrupts the circuit. In its normally closed position, the lower portion 134 closes the circuit extending from switch 116. When switch 134 is open, the circuit is broken and reset button 136 must be pushed to reestablish the circuit. When the react button is pushed, the circuit is operative and closed because the reset button connects contact points 137a and 137b. Two-pole switch 132 is controlled by self-activating relay 138. When reset button 136 is momentarily closed, relay 138 is activated so as to close contacts 133 and 134. When moisture is detected and the transistors 108 and 110 are activated, the signal from the transistors causes relay 138 to open contacts 133 and 134.

Buffer pump 4 is directly powered by the power means of the above detection and output circuitry. The power means is a 115-volt AC electrical source. A plug 140 connects the detection and output circuitry to the electrical source. A single-throw switch 142 connects the power means 140 with the detection and output circuitry. No current flow with the switch in open position. With the switch 142 in closed position, the current flows from the plug 140 to fuse 144. Fuse 144 serves to prevent overloads in the circuitry. When switch 142 is closed, lamp 146 is illuminated by the current flowing through the circuit. Lamp 146 is simply an on-off indicator. The lines 148 and 150 establish the output circuitry for buffer pump 4 from the power means. A plug receptacle 152 is included on line 148 so that the plug on electrical cable 39 from pump 4 can be inserted therein. By connecting the pump to the output circuitry, the pump can be activated or deactivated in response to spillage from the fractionator. Switch 154 is also included on the output circuitry for the buffer pump. In normally closed position, the switch 154 permits the pump 4 to operate as usual. Switch 154 is controlled by self-activating relay 156. When moisture is detected by the sensing means 36, transistors 108 and 110 transmit a signal to relay 156 so as to open switch 154 and deactivate pump 4.

The electrical circuitry of the present invention is connected to plug 140 and the power means across the primary of step-down, magnetic core, non-saturating transformer 160. The secondary of transformer 160 has its conductors connected to the electrodes 46 of sensing means 36.

FIG. 6 is a schematic representation of the remote audio alarm of the fraction spillage detector. This audio alarm is designed, in connection with the output circuitry, to warn persons of the presence of spillage within receiving means 34. As a remote alarm, it will signal those who are far removed from the actual fractionation. Upon the activation of the audio alarm, a person operating the fractionation is given an opportunity to correct the problems which have caused the spillage.

The alarm is attached to the output circuitry by inserting plug 170 into receptacle 122. The conductor line from the alarm to the plug 170 can be as long as desired in order to provide for the remote location of the alarm.

The audio alarm circuitry is activated when relay 114 of the output circuitry is activated. This relay 114 switches a certain amount of voltage from the output circuitry to the alarm circuitry. This voltage passes to differential Zener circuit 172 which works to reduce the voltage to a level necessary to drive the "flasher" integrated circuits 174. The Zener diodes 176 and 178 are in series with resistors 180 and 182, respectively. These resistors 180 and 182 limit the amount of current flowing to the diodes so as to prevent the burnout of the diodes and to cause the rated voltage of the Zener diodes to be developed. In this embodiment, diode 176 is a 3.3 V Zener and diode 178 is a 5.1 V Zener. These diodes serve to reduce the alarm voltage to approximately 1.8 volts. This voltage passes from the Zeners to the integrated circuits 174.

Integrated circuits 174 comprise two LM3909 circuits. Circuit 174 produces an irritating siren-like tone so as to command the operator's attention. The signal passes from the integrated circuits 174 to transistor 184. The emitter of transistor 184 is grounded through a filter/integrator including a capacitor 186 and a resistor 188 arranged in parallel. The collector of transistor 184 is connected to loudspeaker 190 and serves to amplify the audio signal from integrated circuits 174 to a level usable by speaker 190. This speaker 190 may be installed in a suitable location to warn of the occurrence of spillage in the fractionator.

The operation of the described embodiment of the present invention during liquid spillage is believed to be clearly apparent and is briefly summarized at this point. In operation, the fraction spillage detector is connected to a conventional 115 volt electrical outlet of the facility housing the liquid chromatography system. The current passes from plug 140 to closed switch 142 and to lamp 146. Lamp 146 will indicate that the present invention is operative. In the absence of liquid in the spillage in the spillage receiving means 34 and the sensing means 36, the current passes through lines 148 and 150 so as to provide power to plug receptacle 152. Pump 4 is electrically connected to the power through the 152. Thusly, the pump 4 is operative from the output circuitry of the fraction spillage detector. Similarly, the 115 volt outlet is the immediate source of current which energizes solenoid circuit 130 through points 192 and 194. When the solenoid is energized, movable core 68 retracts toward solenoid housing 67. This removes the closure pressure from the pliable conduit 22. As a result of this energizing of the pump 4 and the solenoid 130, the liquid chromatography system flows freely from main column 20 to detector 24 and fractionator 28.

The current from the power source passes through step-down transformer 160. From this transformer 160, current flows to connection points 100 and 102. Points 100 and 102 connect with the positive and negative polarity electrodes 46 of the sensing means 36. In the absence of moisture or liquid in sensing means 36, no current flows between the positive and negative electrodes 46. This makes transistor 106 conductive. Consequently, relays 114, 138, and 156 are not activated and switches 116, 132, and 154 remain in their normal position.

Malfunctions occasionally occur during liquid chromatography activities. These malfunctions, such as power loss, fractionator malfunctions, or component detector problems, can cause inadvertent spillage from the fractionator. For example, if the tube holder 32 fails to index properly upon the signal from the component detector 24, then the tube 30 will overflow and spillage will result. Similarly, during power loss, the sample effluent will continue to empty even though the detector does not work and the fractionator fails to index. The present invention operates to prevent the loss or dilution of the sample effluent in the event of such malfunction by retaining the sample in the main column 20.

As previously noted, spillage receiving means 34 covers the surface area of potential spillage, that is, it is generally longer and wider than the tube holder 32. The sensing means 36, consisting of alternating electrodes 46 of opposing polarity, is located within this receiving means 34 and below tube holder 32. When spillage occurs from a tube in fractionator 28, the filter paper 54 covering electrodes 46 will become wet. The filter paper 54 serves to spread the liquid so as to establish contact between the electrodes of opposing polarity. The moisture in sensing means 36 will provide conductivity for current flow between the electrodes 46. This current flow passes through wires 52 to the detection circuitry. As a result of the conductivity between the electrodes, the current is shunted from base to ground causing transistor 106 to become non-conductive.

The cut-off state of transistor 106 causes transistors 108 and 110 to turn on. The current flowing through transistors 108 and 110 activates relay 114, thereby causing double-throw switch 116 to switch from its normal position. In its new position, switch 116 activates alarm 118 causing glow lamp 120 to shine and connected remote speaker 190 to sound. This provides an audio and a visual signal of the malfunction with the liquid chromatography system.

The shift of switch 116 sends a signal to relay 138 causing the opening of two pole switch 132. The opening of the upper portion 133 of switch 132 creates an open circuit causing solenoid circuit to become deactivated. Upon deactivation, spring 70 causes the movable core 68 to move outwardly from the interior of the solenoid housing 67. The movement of core 68 is translated to the plunger 80. As a result, the end 98 of plunger 80 is forced against pliable conduit 22. This squeezes the conduit 22 so as to stop the flow of liquid from main column 20. The sample effluent is maintained within the column, without dilution, contamination, or significant loss of component resolution.

The opening of the lower portion 134 of two-pole switch 132 activates reset button 136. In other words, the opening of the lower portion 134 creates an open circuit, thereby cutting off the current in that circuit. Current will not flow through that circuit until the reset button is depressed so as to establish contact across points 137a and 137b. The device is not capable of self-activation until the self-holding relays 138 and 156 are reactivated by depressing the reset button 136. This prevents the start-up of the flow of liquid and consequent spillage when the moisture dries on the filter paper 54 of the sensing means 36.

The shift of switch 116 also sends a signal to relay 156 causing the opening of switch 154 in the buffer pump circuit. The opening of the switch 154 creates an open circuit causing the pumps 4 to become deactivated. The deactivation of the pumps 4 prevents excess solvent from being pumped from the reservoir 2 to the main column 20. It also prevents excess pressure from building up in the liquid chromatography system. As before, the circuit to the buffer pumps will not be capable of self-activation until reset button 136 is depressed.

The system remains inactive until an attendant corrects the malfunction and presses the reset button. It will probably be necessary to replace the wet filter paper 54 with dry filter paper so as to prevent conductivity between the electrodes upon resetting the system. Upon the correction of the malfunction, the chromatography activities may continue from the point of interruption.

The fraction spillage detector is somewhat similarly operable in the event of power loss. When power loss occurs, current stops flowing through the system, thereby causing the solenoid circuit 130 to become deactivated and the pliable conduit 22 to be clamped closed. Similarly, a power loss will deactivate the buffer pumps 4 because the pumps are connected directly to the power source of the spillage detector. The audio and visual alarms, however, will not be operable in the event of power loss.

An alternative embodiment of the solenoid means 60 of the present invention is illustrated in FIGS. 7 and 8. While the previously described embodiment effectively illustrates the operation of the fraction spillage detector, the present embodiment offers many advantages to the previously described arrangement. In this embodiment, solenoid 200 and support structure 202 are rigidly mounted to base 204. Solenoid 200 is a Guardian 4HD-CONT-110D solenoid electrically connected to the output circuitry means of FIG. 5. Solenoid 200 is mounted to base 204 by legs 206. As in the embodiment shown in FIG. 4, solenoid 200 includes a housing 208, a movable core 210, a spring 212, and a washer 214. Spring 212 is interposed between fixedly mounted washer 214 and the end of the solenoid housing 208. The spring 212 provides the necessary force to draw movable core 210 from housing 208 when the current is removed from the solenoid 200. A plunger 216 is an integral extension of core 210. Plunger 216 also includes pin 218 mounted therein or thereon. Pin 218 extends a distance beyond the diameter of plunger 216 in a horizontal plane so as to accommodate a slot on stainless steel rod 220.

Support structure 202 extends vertically from base 204 a distance greater than the height of solenoid 200. The top portion 222 of the support structure 202 includes a borehole 224 extending through the width of the top portion. Borehole 224 is of such a size as to accommodate pliable conduit 22. Conduit 22 extends from main column 20, through borehole 224, and to component detector 24. Top portion 222 also has a vertical slot 226 milled transverse to and through borehole 224 so as to accommodate the diameter of rod 220. This slot 226 has a wall 227 which is tangential to the diameter of borehole 224. A portion of conduit 22 extends across slot 226. The top portion 222 has a hole 228 extending in the same direction as borehole 224 at a location slightly above the borehole. This hole 228 is of such a diameter so as to receive pivot member 230.

Stainless steel rod 220 is rotatably mounted at its upper end to pivot member 230. Rod 220 extends downward through slot 226 at an angle such that the rod is generally tangential to the outer diameter of conduit 22. The lower end of rod 220 includes a slot 232 aligned vertically with the length of the rod of a size to rotatably engage pin 218 of plunger 216. As the plunger 216 moves inwardly or outwardly, the pin 218 will move a corresponding distance within slot 232. As a result, the rod 220 will rotatably move about pivot member 230.

A bracing bar 234 is pivotally mounted to shoulder 236 of support structure 202. This bracing bar 234 is shaped to receive the diameter of rod 220. A notch 238 is included on rod 220 to similarly receive bracing bar 234. The bracing bar 234 serves to hold the plunger 216 back when the fraction spillage detector is not in use.

In operation, this alternative embodiment shuts off the liquid flow in a manner somewhat similar to the previous embodiment. If there is no spillage on sensing means 36, then the solenoid 200 has current flowing through it which, in turn, retracts movable core 210 toward housing 208. This motion is transmitted through plunger 216 and pin 218 to rod 220. As the plunger retracts, rod 220 moves angularly in a counterclockwise direction about pivot 230. This movement opens conduit 22 for liquid flow.

In the presence of moisture in the sensing means, the solenoid 200 is deactivated. The spring 212 causes the core 210 and plunger 216 to move from the housing 208. This induces a clockwise motion to rod 220 about pivot 230. The outer diameter of rod 220 exerts a compressive force on conduit 22, thereby closing the conduit and preventing liquid from flowing therethrough. This embodiment provides more force at the point of conduit compression without developing a shearing force on the conduit. This aids in preventing damage to the pliable conduit 22. Also, by using the poor heat conducting stainless steel rod instead of the solenoid-plunger arrangement, the sample flowing through the conduit is protected from the effects of the solenoid heat.

Thus, through the embodiments of the present invention, loss or dilution of sample effluent in the event of fractionator malfunction is prevented. The present invention maintains the sample effluent within the main column, without dilution, contamination, or significant loss of component resolution. The cost benefits and advantages of this device are obvious when valuable and possibly unique samples must be fractionated.

The fraction spillage detector is useful with a variety of liquid chromatography systems. In particular, the spillage detector may be used in combination with simple gravity fed chromatography systems. In gravity fed systems, column flow may be induced by hydrostatic pressure. In such arrangements, there is no need for buffer pumps to support the flow of fluid. Furthermore, gravity fed systems do not require the use of filtration devices, injection ports, and other accessories as shown in the embodiments of this invention. The fraction spillage detector is flexible and adaptable to the simplest and most complex of liquid chromatography systems.

While particular embodiments of the present invention and the method of use thereof have been shown and described, it is evident that there are many changes that may be made, particularly in the electronic circuitry thereof, without departing from the true scope and spirit of the invention. Therefore, it is intended that the scope of the invention be limited only by the claims which follow.

We claim:

1. A spillage detector device for use in conjunction with fractionation in liquid chromatography systems, said device comprising:

a spillage receiving means beneath said fractionation for collecting said spillage;

sensor means including a plurality of electrodes of alternating polarity mounted within said receiving means, said electrodes being conductive in the presence of said spillage;

detection circuit means operatively connected to said sensor means, said detection circuit means being responsive to conductivity between said electrodes of alternating polarity;

pliable circuit means for containing the liquid flow within said liquid chromatography system;

electrically actuated solenoid means for on/off control of liquid flow through said liquid chromatography system, said solenoid means including a support structure and a rod, said support structure including a passageway permitting said pliable conduit to pass therethrough, said rod being pivotally mounted to said support structure and said plunger, said rod being positioned so as to provide compressive closure of said pliable conduit upon motion of said plunger;

output circuitry means operatively connected to said detection circuit means and said solenoid means for deactuating said solenoid means and thus halting liquid flow in response to the presence of liquid spillage about said spillage receiving means; and power means for providing electrical current for powering said sensor means, said detection circuit means, said solenoid means, and said output circuitry means.

2. The device of claim 1 further comprising alarm means operatively connected to said output circuitry means for providing a humanly preceivable signal upon the presence of liquid spillage about said receiving means.

3. The device of claim 2, said alarm means being an electrically actuated audible device.

4. The device of claim 2, said alarm means being a signal light.

5. The device of claim 1 further including channel means, said channel means having said pliable conduit transversely extending therethrough such that a portion of said conduit passes through said channel means, said channel means being in mating relationship with said plunger of said solenoid means.

6. The device of claim 1, said sensor means further including absorbent material covering said electrodes.

7. The device of claim 6, said absorbent material being filter paper permeated with a liquid soluble conductive chemical.

8. The device of claim 1, further including reset means operatively connected to said detection circuit means and said output circuit means, said reset means preventing reactivation of said sensor means and said solenoid means until said reset means is manually activated.

9. The device of claim 1, further including pump means operatively connected to said output circuitry, said pump means for assisting liquid flow through said liquid chromatography system.

10. The device of claim 9 wherein said output circuitry means also deactivates said pump means in response to the presence of spillage about said receiving means.

* * * * *